United States Patent [19]
Sampino et al.

[11] Patent Number: 6,093,386
[45] Date of Patent: Jul. 25, 2000

[54] SHAVING AND SKIN CONDITIONING LOTION

[76] Inventors: Andrew Sampino; Anthony Sampino, both of 159-11 78th St., Howard Beach, N.Y. 11414

[21] Appl. No.: 09/275,990

[22] Filed: Mar. 25, 1999

[51] Int. Cl.[7] ............................................. A61K 7/15
[52] U.S. Cl. ............................................... 424/73
[58] Field of Search ............... 424/73, 401, 70.13, 424/70.17, 70.1

[56] References Cited

U.S. PATENT DOCUMENTS

| | | | |
|---|---|---|---|
| 4,946,870 | 8/1990 | Partain, III et al. | 514/777 |
| 5,512,199 | 4/1996 | Kahn et al. | 252/106 |
| 5,674,480 | 10/1997 | Sampino et al. | 424/70.13 |

*Primary Examiner*—James M. Spear
*Attorney, Agent, or Firm*—Goldstein & Canino

[57] ABSTRACT

A method of conditioning human skin, especially to prepare an area of skin for shaving. A solution comprising chitosonium pyrrolidone carbonxylate in water is applied to the skin, preferably by spraying the solution directly onto the skin. The solution conditions the skin and coats hairs on the skin, making shaving effortless, painless, and irritation free, as well as prolonging the useful life of the shaving blade.

1 Claim, 1 Drawing Sheet

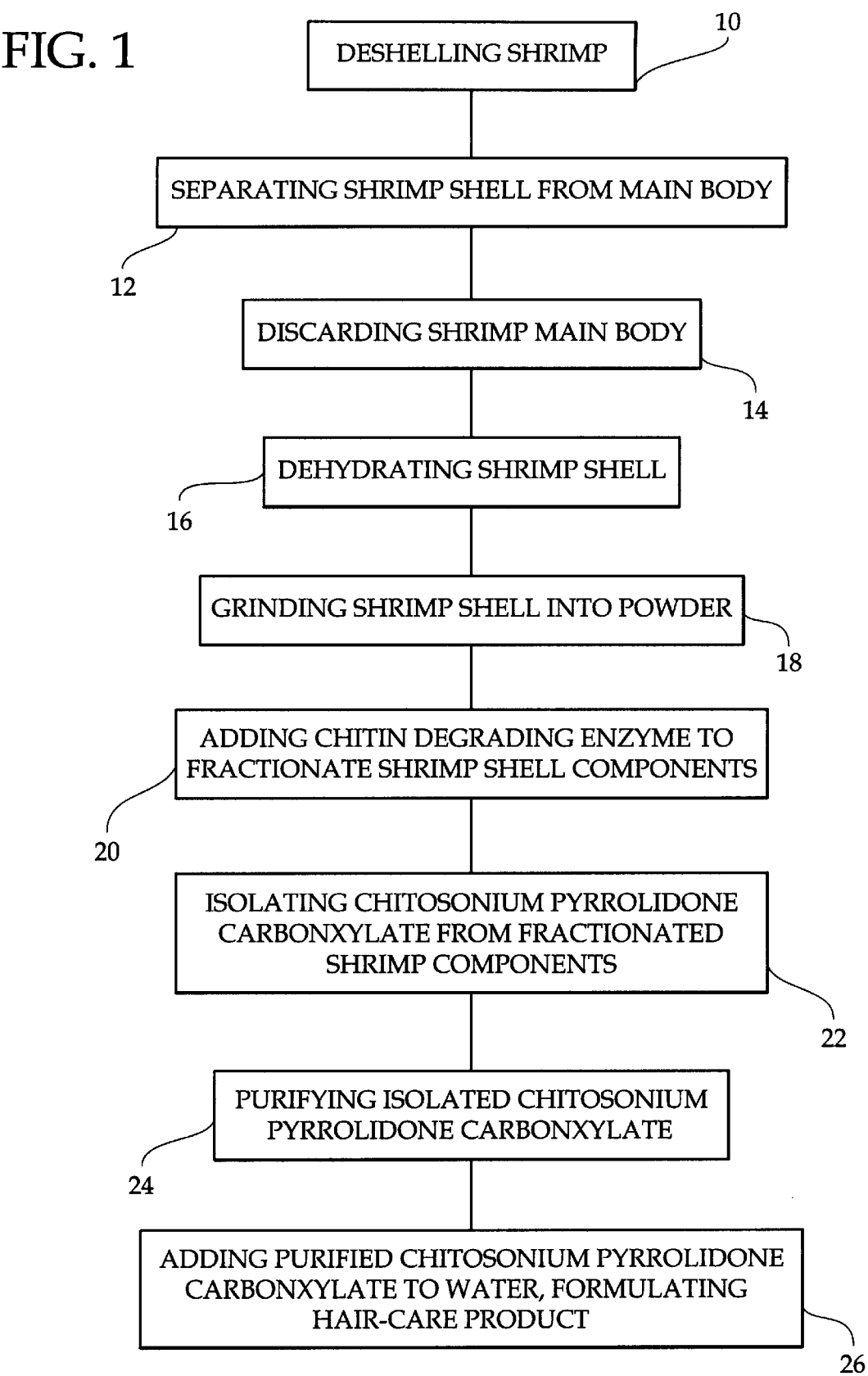

SHAVING AND SKIN CONDITIONING LOTION

BACKGROUND OF THE INVENTION

The present invention discloses a new use of an active ingredient in shaving and skin conditioning products, namely Chitosonium pyrrolidone carbonxylate (the active ingredient). The active ingredient is natural, is derived from shell-fish such as shrimp, and is mixed at approximately 0.01% to 2% in water, the preferred range being 0.3–0.5%

A variety of products have been developed which condition the skin, especially for use just prior to, and during shaving. These products contain a variety of additives, such as aloe, lanolin, and the like to effect softening of the skin. Unfortunately many of these products fail to properly prepare the hair for shaving.

SUMMARY OF THE INVENTION

The present invention possesses several new and beneficial characteristics. Namely, the invention may be utilized as a shaving lotion since the composition makes hair slippery as well as conditions the skin to prepare for shaving. It allows a hair-cutting razor to effortlessly slice through the hair without resistance. Application of this product prior to shaving also prevents wear to razor blades, allowing them to maintain their sharpness for a longer period of time.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a is a diagrammatic flow chart of a method by which chitosonium pyrrolidone carbonxylate is extracted from shrimp.

DETAILED LIST OF REFERENCE NUMERALS UTILIZED IN THE DRAWING

10—de-shelling shrimp 10 by inserting a de-shrimping tool between shrimp main body and shrimp shell, thus, cracking and simultaneously separating shrimp shell from main body 12—separating shrimp shell from main body 12 by securely adhering shrimp shell in a stable position and simultaneously adhering shrimp main body in a movable position such that when said shrimp main body and said shrimp shell are pulled in opposite directions both shell and main body separate 14—discarding shrimp main body 14

16—dehydrating shrimp shell 16 by desiccating said shell utilizing common methods to one skilled in the art such as low intensity heat for a prolonged time period and/or use of dehydrating materials such as salt and anhydrous silicone crystals 18—grinding shrimp shell into powder 18 utilizing common methods to one skilled in the art such as mortar and pestle and like equivalents 20—adding chitin degrading enzymes 20 such as chitinaze which enzymatically fractionates shrimp shell into its individual components 22—isolating chitosonium pyrrolidone carbonxylate from fractionated shrimp components 22 utilizing common methods to one skilled in the art such as absorbent techniques such as lectin absorbent and monoclonal antibodies and/or elusion column 24—purifying isolated chitosonium pyrrolidone carbonxylate 24 utilizing common methods to one skilled in the art such as absorbent techniques such as lectin absorbent and monoclonal antibodies and/or elusion column 26—adding purified chitosonium pyrrolidone carbonxylate to water, formulating hair-care product 26 utilizing common methods to one skilled in the art such as homogenization

DETAILED DESCRIPTION OF THE PREFERRED EMBODIMENTS

Referring to FIG. 1 which is a diagrammatic flow chart of a method by which chitosonium pyrrolidone carbonxylate is extracted from shrimp, the following steps are illustrated: de-shelling a shrimp 10 by inserting a de-shrimping tool between said shrimp main body and shrimp shell, thus, cracking and simultaneously separating said shrimp shell from main body; separating shrimp shell from main body 12 by securely adhering shrimp shell in a stable position and simultaneously adhering shrimp main body in a movable position such that when said shrimp main body and said shrimp shell are pulled in opposite directions both shell and main body separate; discarding shrimp main body 14; dehydrating shrimp shell 16 by desiccating said shell utilizing common methods to one skilled in the art such as low intensity heat for a prolonged time period and/or use of dehydrating materials such as salt and anhydrous silicone crystals; grinding shrimp shell into powder 18 utilizing common methods to one skilled in the art such as mortar and pestle and like equivalents; adding chitin degrading enzymes 20 such as chitinaze which enzymatically fractionates shrimp shell into its individual components; isolating chitosonium pyrrolidone carbonxylate from fractionated shrimp components 22 utilizing common methods to one skilled in the art such as absorbent techniques such as lectin absorbent and monoclonal antibodies and/or elusion column; purifying isolated chitosonium pyrrolidone carbonxylate 24 utilizing common methods to one skilled in the art such as absorbent techniques such as lectin absorbent and monoclonal antibodies and/or elusion column; and adding purified chitosonium pyrrolidone carbonxylate to water, formulating hair-care product 26 utilizing common methods to one skilled in the art such as homogenization.

Additional non-essential ingredients such as preservatives like parabin (methyl, propyl or butyl), DMDM hydantons, fragrances, emulsifiers, colors, and surfactants (shampoo) may be added prior to said homogenization step.

It will be understood that each of the elements described above, or two or more together, may also find a useful application in other types of constructions differing from the type described above.

Advantageously, the product may be applied to the surface which is intended to be shaved either directly or by aerosol or pump spray. The product may be applied immediately prior to shaving. When thus applied, the hair develops a slippery texture which allows effortless cutting by a razor. The preferred method of application involves wetting the facial or body hair which is to be shaved and then applying the product by spraying it on the hair. The hair is then ready for shaving. Thus, according to the inventive method, the composition is used as a substitute for typical shaving creams and gels. Although similar chemicals may have been used along with other ingredients in shampooing and conditioning products used on hair, it is contrary to the known properties of the active ingredient of the invention that it would be suitable as a shaving agent. Thus it is contrary to expectations that the active ingredient, chitosonium pyrrolidone could be used as a shaving lotion.

In addition, the product may be utilized as a relaxer of certain facial hairs. For instance, a man having a full beard or mustache might use the product to alleviate facial irritation which commonly accompanies new facial hair growth, by spraying the product upon said facial hair to relax and soften it.

In conclusion, herein is presented a novel use for chitosonium pyrrolidone carbonxylate in a simple water solution, as a shaving lotion.

What is claimed is:

1. A method of shaving an area of human skin having hairs, using a solution of 0.01 to 2 percent chitosonium pyrrolidone carbonxylate in water and further using a blade, comprising the steps of:

wetting the skin;

conditioning the skin and coating the hairs by applying the solution to the skin at the area to be shaved; and then shaving the area using the blade.

* * * * *